United States Patent [19]

Spielvogel et al.

[11] Patent Number: 5,286,853
[45] Date of Patent: Feb. 15, 1994

[54] BORON-GADOLINIUM COMPOUNDS AND METHOD OF CONDUCTING IMAGING AND/OR NEUTRON CAPTURE THERAPY WITH SAME

[75] Inventors: Bernard F. Spielvogel, Cary; Anup Sood, Durham, both of N.C.

[73] Assignee: Boron Biologicals, Inc., Raleigh, N.C.

[21] Appl. No.: 943,920

[22] Filed: Sep. 11, 1992

[51] Int. Cl.$^5$ .............................................. C07F 5/02
[52] U.S. Cl. ................................................... 534/16
[58] Field of Search ................ 534/16, 0; 540/465; 556/7; 514/64

[56] References Cited

U.S. PATENT DOCUMENTS 4,516,535 5/1985 Russell, Jr. et al. .................. 128/1.1
4,959,356 9/1990 Miura et al. ............................ 514/64

OTHER PUBLICATIONS

Brugger, et al., "Evaluation of Gd-157 As a Neutron Capture Therapy Agent" *Strahlenther Onkol.* 165 (1989), 153-156.
Dischino, et al., "Synthesis of Nonionic Gd Chelates Useful as Contrast Agents for MRI", *Inorg Chem* 30 (1991), 1265-1269.
Takagaki Masao, et al, "Gadolinium Neutron Capture Therapy for Brain Tumors—Biological Aspects," Springer-Verlag, Tokyo, 1991, pp. 494-499.
Shih, J. A., et al. "Progress in Neutron Capture Therapy for Cancer" (Allen, B. J., et al, eds.) Plenum Press, New York, 1992, pp. 183-186.
Allen, B. J., et al "Neutron Capture Therapy With Gadolinium-157," Strahlenther. Onkol. 165 (1989), 156-157 (No. 2/3).

*Primary Examiner*—Robert L. Stoll
*Assistant Examiner*—Lara E. Chapman
*Attorney, Agent, or Firm*—Steven J. Hultquist

[57] ABSTRACT

A gadolinium (3+) complex of polyamine polyacetate, comprising a polyamine nucleus having a pendant boron-containing substituent on one of the nitrogen or carbon atoms of the polyamine nucleus. The boron-gadolinium compound may suitably be of the formula:

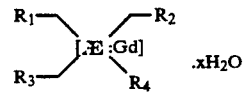

wherein:
 is a polyamine coordination structure capable of covalently bonding the substitutents $R_1$, $R_2$, $R_3$ and $R_4$ and of complexing with Gd;
$R_1$, $R_2$, and $R_3$ are independently selected from carboxyl, carboxylic salt groups, carboxylic ester groups, and carboxylate anion;
$R_4$ is a boron-containing group; and
x is a number from zero to 4.

Also disclosed is a method of treating a tumor-bearing mammalian subject by boron neutron capture therapy wherein the boron drug employed in such treatment comprises a boron-gadolinium compound, and a method of conducting sequential imaging and NCT treatment of a tumor tissue site in the corporeal structure of a mammalian subject, comprising administering to the mammalian subject an MRI imagingly- and NCT treatingly-effective amount of an effective boron-gadolinium compound, visualizing the tumor tissue site by MRI, and treating the tumor tissue by NCT.

12 Claims, No Drawings

BORON-GADOLINIUM COMPOUNDS AND METHOD OF CONDUCTING IMAGING AND/OR NEUTRON CAPTURE THERAPY WITH SAME

BACKGROUND OF THE INVENTION

1. Field of the Invention

This invention relates to novel boron-gadolinium compounds, and to a method of conducting imaging processes and/or neutron capture therapy with boron-gadolinium compounds.

2. Description of the Related Art

Interest in the Neutron Capture Therapy (NCT) of cancer has increased tremendously in recent years. A number of compounds are already in preclinical or clinical trials in the U.S., Europe, Japan, and Australian. Most of these studies are based on the use of $^{10}B$ as the neutron capture agent. Although $^{10}B$ has certain advantages (e.g., versatile chemistry, cost-effectiveness, type of radiation generated upon neutron capture, etc.) over other potential neutron capture agents, there are also some problems. For example, the boron concentrations in tissues are difficult to measure and noninvasive determination of boron distribution in the body is very difficult. Additionally, boron compounds in general have given poor tumor to blood ratio in the past, with some notable exceptions.

Recently, reports have described the use of $^{157}Gd$ compounds as neutron capture agents. Gadolinium-157 has a much larger cross-section for thermal neutrons than boron-10 (66 times larger), and some Gd complexes have been shown to give good tumor to blood and tumor to tissue ratios.

A significant property of $^{157}Gd$ is that, being paramagnetic, it is a very good contrast agent for imaging by magnetic resonance. In fact, one Gd complex is already in clinical use as an MRI agent.

However, as in the case with boron-10, gadolinium-157 also has certain disadvantages as a neutron capture agent. The gadolinium complexes are less potent and can be more toxic due to the type of radiation ($\gamma$-radiation) generated upon neutron capture.

Therefore, a combination of $^{10}B$ and $^{157}Gd$ might compensate each isotope's weaknesses and offer a better therapeutic method of treatment. A single agent incorporating both $^{10}B$ and $^{157}Gd$ may therefore provide not only the diagnostic capability of detecting the tumor, but at the same time a better means of destroying the tumor by both $^{10}B$-NCT and $^{157}Gd$-NCT.

NCT is based on the nuclear reaction produced when a neutron capture agent such as $^{10}B$ or $^{157}Gd$ isotope (localized in tumor tissues) is irradiated with low energy thermal neutrons. The radiation produced is capable of effecting selective destruction of tumor cells while sparing normal cells. The advantage of NCT is the fact that it is a binary system, capable of independent variation of control of the neutron capture agent and thermal neutrons.

While a number of nuclei have high cross section for thermal neutrons, most of the studies have been focused on the use of $^{10}B$ as the neutron capture agent. It would therefore be an advance in the art, and is an object of this invention to provide NCT agents with both $^{10}B$ and $^{157}Gd$ in the same compound.

Boron-10 has a high cross-section (3838 barns) for thermal neutrons. The reaction products of $^{10}B$ and thermal neutrons have short path length and the high linear energy transfer (LET) radiation (LET>100 KeV/$\mu$m) is deposited within the cell giving preferential destruction if the boron is localized in the tumor.

Another advantage of $^{10}B$ is that the chemistry of boron is very versatile and a variety of boron compounds can be readily synthesized. However, the problems with boron compounds are: 1) most of the compounds studied so far give poor tumor to blood ratio, although there are notable exceptions, e.g., boronated porphyrins; 2) boron distribution in the body is difficult to determine without isolating the organs and tissue, and although $^{11}B$ nmr has been used for imaging, it is not very sensitive; and 3) boron concentrations in the tumor are also difficult to determine.

Gadolinium-157 has a much larger cross section (66 times larger than $^{10}B$) for thermal neutrons than boron-10. Gadolinium compounds (due to the presence of unpaired electrons) have been used successfully for NMR imaging and the diethylenetriamine pentaacetic acid complex of $Gd^{3+}$ is currently undergoing clinical trials as an imaging agent. Gd compounds have been shown to provide high tumor concentrations and good tumor to tissue and tumor to blood ratios.

Many Gd complexes behave similar to the corresponding technetium complexes. Therefore, by substituting $^{99m}Tc$ for Gd along with the Gd complex, and by determining the concentration of technetium in various tissues, the concentration of Gd can be estimated. Alternatively, Gd concentrations in various tissues may be determined indirectly by measuring proton relaxivities (MRI).

The disadvantages of Gd are, however, that the major cell killing component of the radiation produced from $Gd^{157}$ and neutron reaction is Auger electrons. To be effective these Auger e's have to be released in the vicinity of the genetic material and this constraint limits the effectiveness of Gd NCT in comparison to $^{10}B$-NCT. A second drawback of the $^{157}Gd$ NCT is that a second component of radiation from $^{157}Gd$-neutron reaction, low LET gamma rays, are not only less effective in killing cells but can also travel longer distances and can destroy normal tissue. On the other hand, delivery of radiation to the surrounding tissue may increase the chance of hitting all the cells in the tumor. Thus a combination of boron-10 and gadolinium-157 may require lower concentration of each component (and decrease side effects) and still be more effective than each individual component at a higher concentration.

Concerning desirable characteristics for imaging reagents generally, the basic properties of good magnetic resonance imaging agents are as follows:

1) Relaxivity: The relaxivity of metal complexes (efficiency with which a complex enhances proton relaxation rate of water) should be sufficiently high. However, an increase of as little as 10-20% in $1/T_1$ could be detected by NMR imaging. Relaxivity may be increased by providing one or more inner sphere coordination site(s) for water molecules.

2) Specificity: For NMR imaging agents it is important that the agent enhances the relaxation rates of target tissue in preference to other tissues. This may be accomplished either by preferential incorporation of compound or by difference in relaxivity if the complex has a higher relaxivity in the environment of one tissue over others.

3) in vivo stability, lack of toxicity and rapid excretability: It is extremely important that the imaging agent has a low acute and chronic toxicity. Many complexes, while inherently nontoxic, could exhibit high toxicity upon dissociation into the free metal ions and ligands. Therefore, both the thermodynamic and the kinetic stabilities of complexes are very important. Additionally, after serving their purpose, diagnostic agents should be excreted within hours of administration. Of course, retention in tumor is highly desirable for NCT.

4) Solubility in water: For ease of delivery, the imaging agent should have good solubility in water.

5) Osmolality: Although not essential, it is beneficial to have uncharged species to prevent hyperosmolality with respect to body fluids.

Considering the desired properties of NCT reagent materials, the properties of good NCT agents are as follows:

1) High cross-section for thermal neutrons: As indicated earlier, both $^{10}B$ and $^{157}Gd$ have high cross-section for thermal neutrons.

2) Tumor specificity: In order for NCT to be effective, the neutron capture agent should preferentially localize into tumor cells. The position inside the cell is also important. So far, this has been one of the most challenging problems for NCT.

3) Stability, Excretability and lack of toxicity: The same criteria apply here as for imaging agents. Not only should the compound have good stability and low toxicity after the treatment (or even before neutron capture reaction), the compound should also be readily excreted from the normal tissue of the body, but retained in tumor cells.

In addition, the criteria of good water solubility and low osomality also apply to NCT agents.

Accordingly, it is one object of the present invention to provide novel boron-gadolinium compounds having utility for imaging applications such as MRI as well as for NCT.

It is another object of the invention to provide a method of making such boron-gadolinium compounds.

It is a further object of the invention to provide a method of and compounds for contemporaneously conducting imaging and NCT processes, utilizing a single reagent formulation.

Other objects and intents of the present invention will be more fully apparent from the ensuing disclosure and appended claims.

SUMMARY OF THE INVENTION

In one broad composition aspect, the present invention relates to boron-gadolinium compounds of the formula:

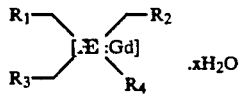

wherein:

Æ is a polyamine coordination structure capable of covalently bonding the substitutents $R_1$, $R_2$, $R_3$ and $R_4$ and of complexing with Gd;

$R_1$, $R_2$, and $R_3$ are independently selected from carboxyl, carboxylic salt groups, carboxylic ester groups, and carboxylate anion;

$R_4$ is a boron-containing group; and x is a number from zero to 4.

In the above-represented boron-gadolinium compound, Æ comprises a coordination structure possessing sufficient coordination sites (at least one, and preferably 6, 7 or 8) to stably complex with the gadolinium atom(s) in the compound. If the coordination number of the coordination structure Æ in the compound is less than 6, the compound, although potentially quite useful in the broad practice of the invention, is less stable than the preferred compounds in which the coordination-number is at least 6. Most preferably, the coordination number is 7 or 8.

In a more specific composition aspect, the present invention relates to boron-gadolinium compounds of the formula:

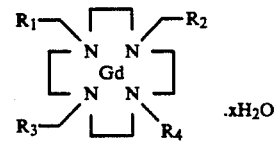

wherein:

$R_1$, $R_2$, and $R_3$ are independently selected from carboxyl, carboxylic salt groups, carboxylic ester groups, and carboxylate anion;

$R_4$ is a boron-containing group; and x is a number from zero to 4.

In boron-gadolinium compounds of the above formula (the term "compounds" herein being broadly construed as inclusive of complexes and coordination structures of varying conformation comprising the Æ nuclear moiety), th boron-containing group $R_4$ may be a borane cage-containing substitutent, as for example of the formula -A$R_5$, wherein A is a divalent linking group such as alkylene, preferably substituted or unsubstituted $C_2$-$C_5$ alkylene, and $R_5$ is a polyborane end group, such as carboranyl:

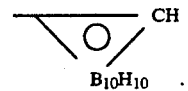

In another aspect of boron-gadolinium compounds within the broad scope of the present invention, the invention contemplates gadolinium (3+) complexes of polyamine polyacetates, wherein the polyamine nucleus has a pendant boron-containing substitutent on one of the nitrogen atoms or carbon atoms of the polyamine nucleus, such as a pharmaceutically acceptable decahydrodecaborane-or dodecarborane-containing pendant group. The macrocyclic polyamine nucleus may for example comprise a cyclen moiety as in compounds illustratively described above. The macrocyclic ligand may for example comprise a ligand such as 1,4,7-tris (carboxymethyl)-10-(1-carboranylpropyl)-1,4,7,10-tetraazacyclododecane or 1,4,7-tris (carboxymethyl)-10-(1-phenylpropyl)-1,4,7,10-tetraazacyclododecane with such phenylpropyl substitutent in the last-mentioned compound being replaceable by any suitable boron-containing groups or moieties.

In a further aspect, the present invention relates to a method of making a boron-gadolinium compound with a boron group substituted on the nitrogen atom of a constituent amine group of a polyamine precursor compound, comprising the steps of:

protecting all of the amine groups of the polyamine except the one where the boron group is to be attached;

reacting such partially protected polyamine with a boron-containing group having a readily displaceable group, e.g., halide, to attach the boron group to the polyamine;

deprotecting the polyamine;

reacting the deprotected polyamine with chloroacetic acid or other suitable chlorocarboxylic acid to form a carboxyl functionalized polyamine; and reacting the carboxyl functionalized polyamine with a gadolinium halide compound to form the boron-gadolinium compound.

In a still further aspect, the invention relates to a method of making a boron-gadolinium compound with a boron group substituted on a carbon atom thereof, from a polyamine starting compound, comprising the steps of:

protecting all of the amine groups of the polyamine starting compound;

generating a carbanion followed by reaction with a suitable substituted boron group;

deprotecting the polyamine;

reacting the deprotected polyamine with chloroacetic acid or other suitable chlorocarboxylic acid to form a carboxyl functionalized polyamine; and reacting the carboxyl functionalized polyamine with a gadolinium halide compound to form the boron-gadolinium compound.

In another aspect, the present invention relates to a method of synthesizing a cyclic polyamine-based boron-gadolinium compound, comprising the steps of:

reacting tetraazacyclododecane with p-toluenesulfonyl chloride to form a corresponding tetraazacyclododecane which is tri-N-substituted with p-toluenesulfonyl chloride;

monoalkylating the tetraazacyclododecane which is tri-N-substituted with p-toluenesulfonyl chloride, by reaction thereof with a carboranylalkylhalide, to yield a corresponding carboranylalkyltetraazacyclododecane which is tri-N-substituted with p-toluenesulfonyl chloride;

converting the carboranylalkyltetraazacyclodidecane which is tri-N-substituted with p-toluenesulfonyl chloride, under acidic conditions, to the corresponding mono-carboranylalkyl-substituted free polyamine;

carboxylating the mono-carboranylalkyl-substituted free polyamine with chloroacetic acid under mildly basic conditions to yield the corresponding monoalkylated tetraazacyclododecanetriacetic acid; and reacting a gadolinium halide hydrate complex with the monoalkylated tetraazacyclododecanetriacetic acid, to form the cyclic polyamine-based boron-gadolinium compound.

In another aspect, the present invention relates to a method of treating a tumor-bearing mammalian subject by neutron capture therapy wherein the drug employed in such treatment comprises a boron-gadolinium compound. The boron-gadolinium complex may for example comprise a gadolinium (3+) complex of a cyclic polyamine polyacetate, wherein the macrocyclic polyamine nucleus has a pendant boron-containing substituent on one of the nitrogen atoms or carbon atoms of the polyamine nucleus. The pendant boron-containing substituent may illustratively comprise a carboranylalkyl group, such as a carboranylpropyl radical. Preferably, the drug employed in such treatment comprises a boron-gadolinium compound of the formula:

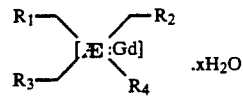

wherein:

is a polyamine coordination structure capable of covalently bonding the substitutents $R_1$, $R_2$, $R_3$ and $R_4$ and of complexing with Gd;

$R_1$, $R_2$, and $R_3$ are independently selected from carboxyl, carboxylic salt groups, carboxylic ester groups, and carboxylate anion;

$R_4$ is a boron-containing group; and x is a number from zero to 4.

In another aspect, the invention relates to a method of treating a patient with a malignant tumor which comprises admininstering to the patient an effective dose of a compound of the formula:

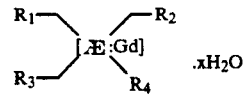

wherein:

Æ is a polyamine coordination structure capable of covalentl bonding the substitutents $R_1$, $R_2$, $R_3$ and $R_4$ and of complexing with Gd;

$R_1$, $R_2$, and $R_3$ are independently selected from carboxyl, carboxylic salt groups, carboxylic ester groups, and carboxylate anion;

$R_4$ is a boron-containing group; and x is a number from zero to 4.

More preferably, such compound is of the formula:

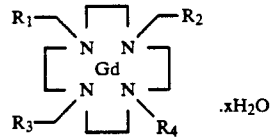

wherein:

$R_1$, $R_2$, and $R_3$ are independently selected from carboxyl, carboxylic salt groups, carboxylic ester groups, and carboxylate anion;

$R_4$ is a boron-containing group; and x is a number from zero to 4.

The effective amount of the compound in the above-described method of treatment is sufficient to accumulate boron and gadolinium in the tumor in a concentration equivalent to at least 10 ppm by weight of boron, based on the weight of tumor-containing tissue. As used herein, such "equivalent concentration" refers to the amount of boron and gadolinium together which generates the same amount of tumor destruction as 10 ppm of boron alone.

Thereafter, the method includes the step of directing at the tumor-bearing tissue a beam of neutrons having an energy distribution effective for neutron capture, for sufficient time to effect substantial tumor tissue deterioration.

In another aspect, the present invention relates to a method of conducting sequential imaging and NCT treatment of a tumor tissue site in the corporeal structure of a mammalian subject, comprising administering to the mammalian subject an MRI imagingly- and NCT treatingly-effective amount of an effective boron-gadolinium compound, visualizing the tumor tissue site by MRI, and treating the tumor tissue by NCT.

Other aspects and features of the present invention will be more fully apparent from the ensuing disclosure and appended claims.

DETAILED DESCRIPTION OF THE INVENTION, AND PREFERRED EMBODIMENTS THEREOF

The present invention is based on the discovery of a class of novel boron-gadolinium compounds which have potential utility for imaging applications, e.g., in MRI, as imaging reagents, by virtue of their gadolinium content, and also have potentially utility as effective NCT reagents, by virtue of their boron and gadolinium content.

Accordingly, these compounds can be employed in a dual-modality treatment regimen for combatting tumors in a tumor-bearing tissue, e.g., in a mammalian subject. After administration to the tumor-bearing mammalian subject, the localization of the reagent in the tumor tissue can be confirmed and measured by MRI visualization techniques, to ensure that there is sufficient amount of the reagent at the tumor tissue site, e.g., an effective amount being sufficient to accumulate boron and gadolinium in the tumor in a boron equivalent concentration of at least 10 ppm by weight, based on the weight of tumor-containing tissue, following which a beam of neutrons, having an energy distribution effective for neutron capture, can be directed at the tumor tissue for sufficient time to effect substantial tumor tissue deterioration.

The separate and independent requirements and characteristics of effective imaging reagents and of effective NCT reagents has been discussed hereinabove in the "Background of the Invention" section hereof. As a result of such separate and distinct efficacy criteria for MRI reagent materials and for NCT reagent materials, it has not been previously recognized that a boron-gadolinium compound could be contemporaneously employed for MRI and for NCT, as carried out in sequential fashion following administration of a single boron-gadolinium reagent material to the patient or mammalian subject.

In this respect, it should be noted that boron compounds per se, i.e., compounds containing boron but not gadolinium, are generally poor imaging reagents for imaging applications such as MRI. Gadolinium compounds, on the other hand, include effective imaging reagents for MRI. In respect of NCT applications, known reagent materials include boron compounds per se. Gadolinium compounds per se, i.e., compounds containing gadolinium but not boron, also have been contemplated by the prior art as NCT reagents. In exposure to neutron flux, however, the neutron capture characteristics and radiation generation characteristics of boron compounds per se differ significantly from the corresponding characteristics of gadolinium compounds per se.

Specifically, in exposure to a beam of neutrons, boron compounds per se generate alpha particle radiation which is of short distance effect-in other words, the radiation from such boron compounds in tissue medium is short-range, being rapidly attenuated within the cellular dimensions of the tissue in which the radiation is generated. By contrast, radiation generated by gadolinium compounds per se, in exposure to neutron beam impingement thereon, comprises gamma radiation which is of long-range character (in comparison to alpha particle radiation) and which is of higher destructive capability and lower selectivity in tissue medium than alpha particle radiation. Accordingly, from considerations of controllability of radiation penetration, and localization of tissue-deteriorating action of the neutron capture-induced radiation, boron compounds per se are generally considered to be markedly superior to gadolinium compounds per se.

In addition to the foregoing distinctions between boron compounds per se and gadolinium compounds per se, other considerations impact the choice and usefullness of reagent compounds for imaging applications and for NCT applications.

For example, to be an effective imaging reagent, a particular compound must have one or more coordination site(s) available for complexing with water.

Further, in vivo usage of any physiologically active compound requires appropriate non-toxicity characteristics, and in gadolinium compounds, toxicity is a function of the availability of gadolinium in the compound, with increasing availability being associated with increasing toxicity. Gadolinium in the +3 oxidation state is particularly toxic, and thus must be very stably complexed when present in a compound employed in pharmaceutical and/or pharmacological applications. Accordingly, the ligands and coordination system associated with the gadolinium in the compound must ensure strong chelation or complexing, so that toxicity side-effects are minimized.

It is apparent from the foregoing that there are many and competing considerations which impact the choice and usefullness of compounds in imaging (e.g., MRI) applications and in NCT applications, and it is not obvious or predictable that a compound which may have efficacy in one such application would be at all suitable in the other such application. In other words, there is no correlative character between the utility and serviceability of compounds for these different end use applications. An example of the prior art evidencing such lack of nexus between imaging reagent compounds and NCT compounds is U.S. Pat. No. 4,959,356, which describes a boron-gadolinium compound only as being useful for boron neutron capture therapy.

More specifically, Miura et al. U.S. Pat. No. 4,959,356 issued Sep. 25, 1990, discloses boronated porphyrin compounds wherein the central nuclear (coordination) atom is a metal selected from the group consisting of zinc, iron, magnesium, manganese, copper, cobalt, germanium, and gadolinium, and these compounds are described as having utility in boron neutron capture therapy applications. There is no teaching or suggestion in Miura et al. that the boron-gadolinium compounds disclosed therein may have any possible usefulness in imaging applications.

Against these various considerations and concerns, the present invention embodies the discovery that compounds containing both boron and gadolinium can be potentially usefully employed for imaging applications as well as for NCT applications, as well as the discovery of compounds adapted for such purpose which have distinct benefits and advantages over the boron-gadolinium compounds of the Miura et al. patent in application to imaging uses as well as NCT.

Depending on the number of carboxyl (—COOH) groups present in the Miura et al. compound, the coordination number of the Miura et al. porphyrins is either 4 or 6. In the carboranyl cyclic polyamine gadolinium compounds forming a preferred class of boron-gadolinium compounds of the present invention, the coordination number of the compound is 7, in consequence of which the inventive compounds retain the central gadolinium atom in the macrocyclic "cage" structure of the cyclen-based complex in a tighter fashion (with correspondingly reduced toxicity) than compounds (complexes) of lower coordination number. As an additional benefit, the resulting compounds are characterized by higher stability than lower coordination number compounds of the prior art.

The novel boron-gadolinium compounds of the present invention include compounds of the formula:

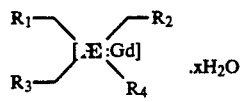

wherein: $Æ$ is a polyamine coordination structure capable of covalently bonding the substitutents $R_1$, $R_2$, $R_3$ and $R_4$ and of complexing with Gd;

$R_1$, $R_2$, and $R_3$ are independently selected from carboxyl, carboxylic salt groups, carboxylic ester groups, and carboxylate anion;

$R_4$ is a boron-containing group; and x is a number from zero to 4.

In the above-represented boron-gadolinium compound, $Æ$ comprises a coordination structure possessing sufficient coordination sites (at least one, and preferably 7 or 8) to stably complex with the gadolinium atoms(s) in the compound. Cyclen-based coordination structures are preferred, but a variety of other polyamines may be potentially usefully employed in the broad practice of the present invention, including linear as well as other cyclic polyamines, e.g., tri-, tetra-, and pentaamines of various structures and conformations, in which the polyamine coordination structure may be a hydrocarbyl polyamine or other type polyamine including various other atomic/elemental constituents, e.g., heteroatoms, to provide a coordination structure to which the carboxylic R-group substituents may be covalently bonded. Preferably, such carboxylic R-groups are covalently bonded to nitrogen atoms or to carbon atoms of the coordination structure $Æ$.

In a more specific composition aspect, the present invention relates to boron-gadolinium compounds of the formula:

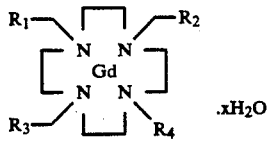

wherein:

$R_1$, $R_2$, and $R_3$ are independently selected from carboxyl, carboxylic salt groups, carboxylic ester groups, and carboxylate anion;

$R_4$ is a borane-containing group; and x is a number from zero to 7.

In boron-gadolinium compounds of the above formulae, the boron-containing group $R_4$ may be a borane cage substituent, as for example a borane group of the formula —$AR_5$, wherein A is a divalent linking group such as alkylene, preferably substituted or unsubstituted $C_2$–$C_5$ alkylene, and $R_5$ is a polyborane end group, such as carboranyl:

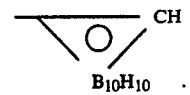

Alternatively, the boron-containing group may for example comprise dodecaborane, boronic acid groups, decahydrodecaborane, dodecahydrododecaborane, etc., and such boron-containing group may optionally be further substituted, as for example by substituents such as halo, hydroxyl, alkyl, amino, etc.

Boron-gadolinium compounds within the broad scope of the present invention may include gadolinium (3+) complexes of linear and cyclic polyamine polyacetates, wherein the polyamine nucleus has a pendant boron-containing substituent on one of the nitrogen atoms or carbon atoms of the polyamine nucleus, such as a decahydrodecaborane- or dodecaborane-containing pendant group. The polyamine nucleus may for example comprise a cyclen moiety as in the compounds described above. The macrocyclic ligand may for example comprise a ligand such as 1,4,7-tris (carboxymethyl)-10-(1-carboranylpropyl)-1,4,7,10-tetraazacyclododecane or 1,4,7-tris (carboxymethyl)-10-(1-phenylpropyl)-1,4,7,10-tetraazacyclododecane with such phenylpropyl substituent in the last-mentioned compound being replaceable by any suitable boron-containing groups or moieties.

The boron-gadolinium compounds of the invention, with a boron group substituted on the nitrogen atom of a constituent amine group of a polyamine precursor compound, may usefully be made by a synthesis process comprising the steps of:

protecting all of the amine groups of the polyamine except the one where the boron group is to be attached;

reacting such partially protected polyamine with a boron-containing group having a readily displaceable group, e.g., halide, to attach the boron group to the polyamine;

deprotecting the polyamine;

reacting the deprotected polyamine with chloroacetic acid or other suitable chlorocarboxylic acid to form a carboxyl functionalized polyamine; and reacting the carboxyl functionalized polyamine with a gadolinium halide compound to form the boron-gadolinium compound.

Correspondingly, boron-gadolinium compounds of the invention, with a boron group substituted on a carbon atom thereof, may usefully be synthesized from a polyamine starting compound, by a synthesis process comprising the steps of:

protecting all of the amine groups of the polyamine starting compound;

generating a carbanion followed by reaction with a suitable substituted boron group;

deprotecting the polyamine;

reacting the deprotected polyamine with chloroacetic acid or other suitable chlorocarboxylic acid to form a carboxyl functionalized polyamine; and reacting the carboxyl functionalized polyamine with a gadolinium halide compound to form the boron-gadolinium compound.

In a specific embodiment, cyclic polyamine-based boron-gadolinium compounds of the invention may be synthesized, by a process comprising the steps of:

reacting tetraazacyclododecane with p-toluenesulfonyl chloride to form a corresponding tetraazacyclododecane which is tri-N-substituted with p-toluenesulfonyl chloride;

monoalkylating the tetraazacyclododecane which is tri-N-substituted with p-toluenesulfonyl chloride, by reaction thereof with a carboranylalkylhalide, to yield a corresponding carboranylalkyltetraazacyclododecane which is tri-N-substituted with p-toluenesulfonyl chloride;

converting the carboranylalkyltetraazacyclodidecane which is tri-N-substituted with p-toluenesulfonyl chloride, under acidic conditions, to the corresponding mono-carboranylalkyl-substituted free polyamine;

carboxylating the mono-carboranylalkyl-substituted free polyamine with chloroacetic acid under mildly basic conditions to yield the corresponding monoalkylated tetraazacyclododecanetriacetic acid; and reacting a gadolinium halide hydrate complex with the monoalkylated tetrraazacyclododecanetriacetic acid, to form the cyclic polyamine-based boron-gadolinium compound.

Set out below, in reference to Schemes 1 and 2, is a more specific discussion of the synthesis of boron-gadolinium compounds of the above-described type.

Scheme 1

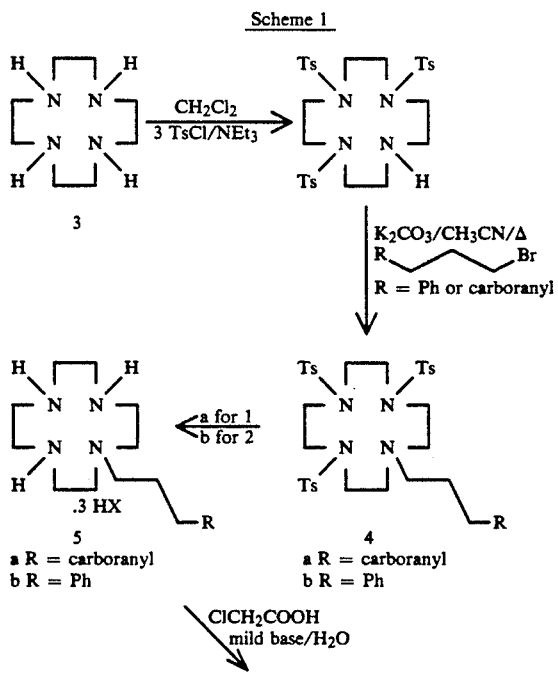

CICH₂COOH
mild base/H₂O

-continued
Scheme 1

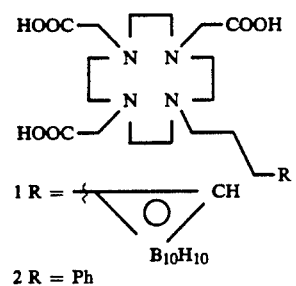

1 R = carboranyl
2 R = Ph a = HBr/AcOH/PhOH/rt
b = i) Na/NH₃/NH₂CONH₂
   ii) HCl In Scheme 1, tetraazacyclododecane, 3, which is commercially available, is converted to the monocarboranylalkyl, 4a, or monophenylalkyl, 4b, polycycle, in two steps. After monoalkylation, the remaining amine nitrogens in the polycycle are deprotected, and the monophenylpropylpolyamine, 5b, is formed. The carboranyl cages, although susceptible to attack by base, are very stable in acid. Once the monosubstituted free polyamines, 5, are obtained, reaction is carried out with 3 equivalents of ClCH₂COOH under mildly basic conditions (NaHCO₃) to give the corresponding monoalkylated-tetraazacyclododecanetriacetic acid. The Gd complexes are prepared by reaction of GdCl₃.6H₂O with the appropriate ligand in pyridine or other suitable solvent, as shown in Scheme 2 below.

Scheme 2

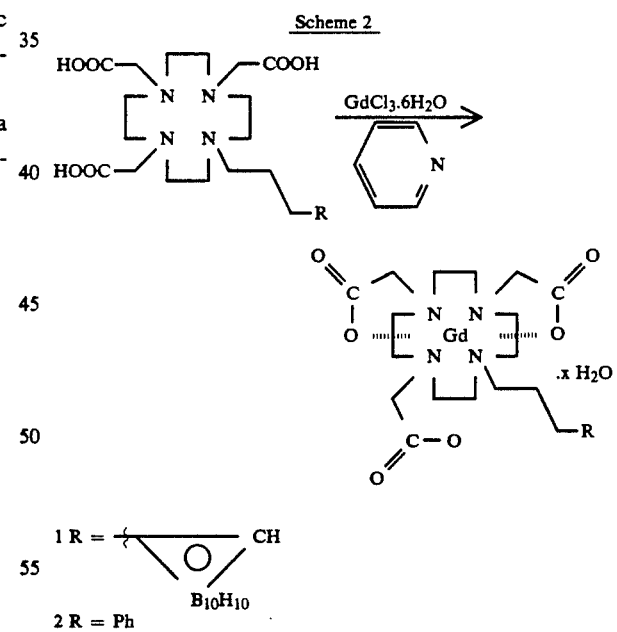

1 R = carboranyl
2 R = Ph

In a treatment aspect, the present invention encompasses a method of treating a tumor-bearing mammalian subject by neutron capture therapy wherein the drug employed in such treatment comprises a boron-gadolinium compound.

The boron-gadolinium complex employed in such treatment may for example comprise a gadolinium (3+) complex of a polyamine polyacetate, wherein the polyamine nucleus has a pendant boron-containing substituent on one of the nitrogen atoms or carbon atoms of the polyamine nucleus. The pendant boron-containing substituent may illustratively comprise a carboranylalkyl group, such as a carboranylpropyl radical. Preferably, the drug employed in such treatment comprises a boron-gadolinium compound of the formula:

$$\begin{array}{c} R_1 \diagdown \quad \diagup R_2 \\ [\text{Æ:Gd}] \\ R_3 \diagup \quad \diagdown R_4 \end{array} \cdot xH_2O$$

wherein:
Æ is a polyamine coordination structure capable of covalently bonding the substitutents $R_1$, $R_2$, $R_3$ and $R_4$ and of complexing with Gd;
$R_1$, $R_2$, and $R_3$ are independently selected from carboxyl, carboxylic salt groups, carboxylic ester groups, and carboxylate anion;
$R_4$ is a boron-containing group; and
x is a number from zero to 4.

Such compound may for example have the formula:

$$\begin{array}{c} R_1 \diagdown \;\ulcorner\;\;\;\urcorner\; \diagup R_2 \\ \;\ulcorner\; N \quad N \;\urcorner\; \\ \quad Gd \\ \;\llcorner\; N \quad N \;\lrcorner\; \\ R_3 \diagup \;\llcorner\;\;\;\lrcorner\; \diagdown R_4 \end{array} \cdot xH_2O$$

wherein:
$R_1$, $R_2$, and $R_3$ are independently selected from carboxyl, carboxylic salt groups, carboxylic ester groups, and carboxylate anion;
$R_4$ is a borane-containing group; and
x is a number from zero to 4.

In another aspect, the invention contemplates a method of treating a patient with a malignant tumor which comprises:
admininstering to the patient an effective dose of a compound of the formula:

$$\begin{array}{c} R_1 \diagdown \quad \diagup R_2 \\ [\text{Æ:Gd}] \\ R_3 \diagup \quad \diagdown R_4 \end{array} \cdot xH_2O$$

wherein:
Æ is a polyamine coordination structure capable of covalently bonding the substitutents $R_1$, $R_2$, $R_3$ and $R_4$ and of complexing with Gd;
$R_1$, $R_2$, and $R_3$ are independently selected from carboxyl, carboxylic salt groups, carboxylic ester groups, and carboxylate anion;
$R_4$ is a boron-containing group; and
x is a number from zero to 4, such effective amount being sufficient to accumulate boron and gadolinium in the tumor in a concentration equivalent to at least 10 ppm by weight of boron per se, based on the weight of tumor-containing tissue; and
directing at the tumor-bearing tissue a beam of neutrons having an energy distribution effective for neutron capture, for sufficient time to effect substantial tumor tissue deterioration.

In another end use application involving dual functional imaging/NCT boron-gadolinium compounds, the present invention is practiceable by a method of conducting sequential imaging and NCT treatment of a tumor tissue site in the corporeal structure of a mammalian subject, comprising administering to the mammalian subject an MRI imagingly- and NCT treatingly- effective amount of an effective boron-gadolinium compound, visualizing the tumor tissue site by MRI, and treating the tumor tissue by NCT.

NCT is typically carried out by injecting the patient with the compound so that it at least partially accumulates in a tumor tissue site. The compound by virtue of it boron and gadolinium components provides elements having isotopes, that capture neutrons and emits radiation to destroy or at least partially deteriorate the cells of the tumor tissue. Effective tumor destruction involves delivery to and accumulation in the tumor cells of the boron and gadolinium elements so that the isoptopes are present at a concentration equivalent to at least about 10 ppm boron per se, based on the weight of the tumor tissue, and preferably at least about 30 ppm boron per se, on the same weight basis.

To provide the aforementioned effective concentrations of the isotopic element at the tumor situs, it is generally desirable to inject the patient with a dose of the compound in the range of from about 2 to about 30 grams of the compound in a pharmacologically and pharmaceutically acceptable formulation, a suitable period of time before neutron beam exposure of the tumor situs, e.g., from about 0.5 to about 30 days beforehand. The dosage form may include a full complement of the compound for the intended neutron beam exposure treatment, or alternatively, portions of the total dose may be sequentially administered to achieve the desired in vivo concentration in the tumor tissue.

The neutron beam generating apparatus may be of any suitable type, as appropriate to the NCT treatment regimen being implemented. Typically, the neutron beam energy distribution and energy flux, and compound dosage will be of such character to allow the accumulation of the isotope in the tumor tissue at a concentration of at least 10 ppm, based on the weight of the tumor tissue, and the neutron beam exposure will be continued for sufficient time to effect substantial tumor tissue deterioration, and preferably substantially complete destruction of such tumor tissue.

While the invention has been described herein in reference to specific embodiments, features and aspects, it will be recognized that numerous variations, modifications, and other embodiments are possible, and the invention therefore is to be broadlly construed as including all such variation, modifications, and other embodiments.

What is claimed is:
1. A boron-gadolinium ($^{10}B$-$^{157}Gd$) compound of the formula

$$\begin{array}{c} R_1 \diagdown \;\ulcorner\;\;\;\urcorner\; \diagup R_2 \\ \;\ulcorner\; N \quad N \;\urcorner\; \\ \quad Gd \\ \;\llcorner\; N \quad N \;\lrcorner\; \\ R_3 \diagup \;\llcorner\;\;\;\lrcorner\; \diagdown R_4 \end{array} \cdot xH_2O.$$

wherein:
$R_1$, $R_2$, and $R_3$ are independently selected from carboxyl, carboxylic salt groups, carboxylic ester groups, and carboxylate anion;
$R_4$ is a boron-containing group; and
x is a number from zero to 7.

2. A compound according to claim 1, wherein $R_4$ is a borane cage substituent.

3. A compound according to claim 1, wherein $R_4$ is a borane cage group of the formula —$AR_5$, wherein A is a divalent linking group, and $R_5$ is a polyborane end group.

4. A compound according to claim 3, wherein A is alkylene.

5. A compound according to claim 3, wherein A is substituted or unsubstituted $C_2$–$C_5$ alkylene.

6. A compound according to claim 3, wherein $R_5$ is selected from the group consisting of pharmaceutically acceptable substituted and unsubstituted carboranyl groups.

7. A compound according to claim 1, wherein $R_4$ is selected from the group consisting of decahydrododecaborane- and dodecaborane-containing pendant groups, and carborane groups.

8. A compound according to claim 1, wherein $R_4$ is carboranylalkyl.

9. A compound according to claim 1, wherein $R_4$ is carboranylpropyl.

10. A compound according to claim 1, wherein x is a number from zero to 4.

11. A composition useful for neutron capture therapy and magnetic resonance imaging, including an active ingredient consisting essentially of a neutron capture therapeutically effective and magnetic resonance imagingly effective amount of a boron-gadolinium ($^{10}$B-$^{157}$Gd) compound of the formula:

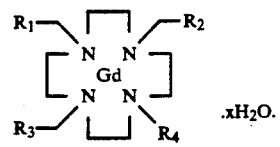

wherein:
  $R_1$, $R_2$, and $R_3$ are independently selected from carboxyl, carboxylic salt groups, carboxylic ester groups, and carboxylate anion;
  $R_4$ is a boron-containing group; and
  x is a number from zero to 7.

12. A boron-gadolinium ($^{10}$B-$^{157}$Gd) compound of the formula:

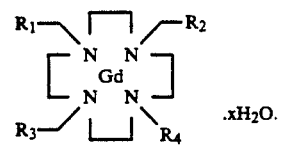

wherein:
  $R_1$, $R_2$, and $R_3$ are carboxyl;
  $R_4$ is carboranylalkyl; and
  X is a number from zero to 7.

* * * * *